US00PP33637P2

(12) United States Plant Patent
Shipley

(10) Patent No.: US PP33,637 P2
(45) Date of Patent: Nov. 16, 2021

(54) DESERT WILLOW TREE NAMED 'BUBBA JONES'

(50) Latin Name: *Chilopsis linearis*
Varietal Denomination: Bubba Jones

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 16/974,137

(22) Filed: Oct. 16, 2020

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216, 226
See application file for complete search history.

*Primary Examiner* — Susan McCormick Ewoldt
*Assistant Examiner* — Karen M Redden

(57) ABSTRACT

A new and distinct *Chilopsis linearis* tree named 'Bubba Jones' is characterized by a naturally multitrunked, rounded, relatively open form, fast growth, dark green leaves and large, pleasantly fragrant flowers with crisped, ruffled corollas with a distinctively bicolored corolla (75A over 72A, 285 R.H.S. Color Chart), blooming throughout the warm season (locally May-October). 'Bubba Jones' can also be used as a rounded, single trunked tree with proper pruning. Low seed production has been noted, beneficial for more flowering and less trash in the landscape.

6 Drawing Sheets

Latin name: *Chilopsis linearis*.
Varietal denomination: 'Bubba Jones'.

INTRODUCTION

*Chilopsis linearis*, commonly known as desert willow, is a large shrub or up to a medium, typically multitrunked tree, occasionally reaching 25 feet tall×40 feet wide in favorable locations such as broad washes. *Chilopsis* is both drought and winter deciduous. Trunk diameters can reach 2-3 feet in diameter, although trees this large are rare. Desert willow grows wild throughout much of the arid and semiarid southwestern United States and northern Mexico up to an elevation of about 6000'. *Chilopsis* stands are most commonly found adjacent to and within normally dry washes. Desert willow has been successfully utilized as a small-medium sized landscape tree throughout much of the southwestern US, tolerating extreme heat combined with low water use. *Chilopsis* is rarely freeze damaged within its region of cultivation. The trees have large trumpet shaped flowers generally produced throughout the warm season as long as moisture is available. Flower color ranges from white to pink to a deep magenta or maroon, depending on the seed source or cultivar. Both large bees and hummingbirds visit the flowers for nectar. A variety of cultivars, some patented, as well as seedling forms are available in the trade.

BACKGROUND OF THE INVENTION

The present invention relates to a new and distinct cultivar of *Chilopsis linearis*. The cultivar originated from a cross between *Chilopsis linearis* 'Bubba' (not patented) and *Chilopsis linearis* 'Warren Jones' (not patented) with 'Bubba' as the female parent and 'Warren Jones' as the male parent. *Chilopsis linearis* 'Bubba Jones' is a selection from the Fi generation of that cross and is the object of this application.

SUMMARY OF THE INVENTION

Among the features that distinguish the new *Chilopsis* cultivar from all other available and commercial varieties of *Chilopsis* known to the inventor are the following combination of characteristics: fast growth, open form, large, bicolored, ruffled flowers (color 75A over 72A) with blooms produced throughout the warm season (locally May-October), and minimal fruit/seed production. Flowers are noticeably and pleasantly fragrant.

The propagation procedure is as follows: Four inch long semi-hardwood cuttings have the lower leaves removed, and then are soaked in 5:1 DIP'N GRO™. Cuttings are placed in peat media in grow trays, then moved to a fog propagation house where they are misted every 30 minutes with the soil temperature maintained between 75-85° F. Rooting is essentially complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant. 'Bubba Jones' was propagated at a commercial nursery near Sahuarita, Ariz., USA.

BRIEF DESCRIPTION OF THE DRAWINGS

The accompanying photographs illustrate *Chilopsis linearis* 'Bubba Jones' growing near Sahuarita, Ariz., depicted in color as nearly correct as it is possible to make in a color illustration of the character.

DETAILED PLANT DESCRIPTION

Figure 1:
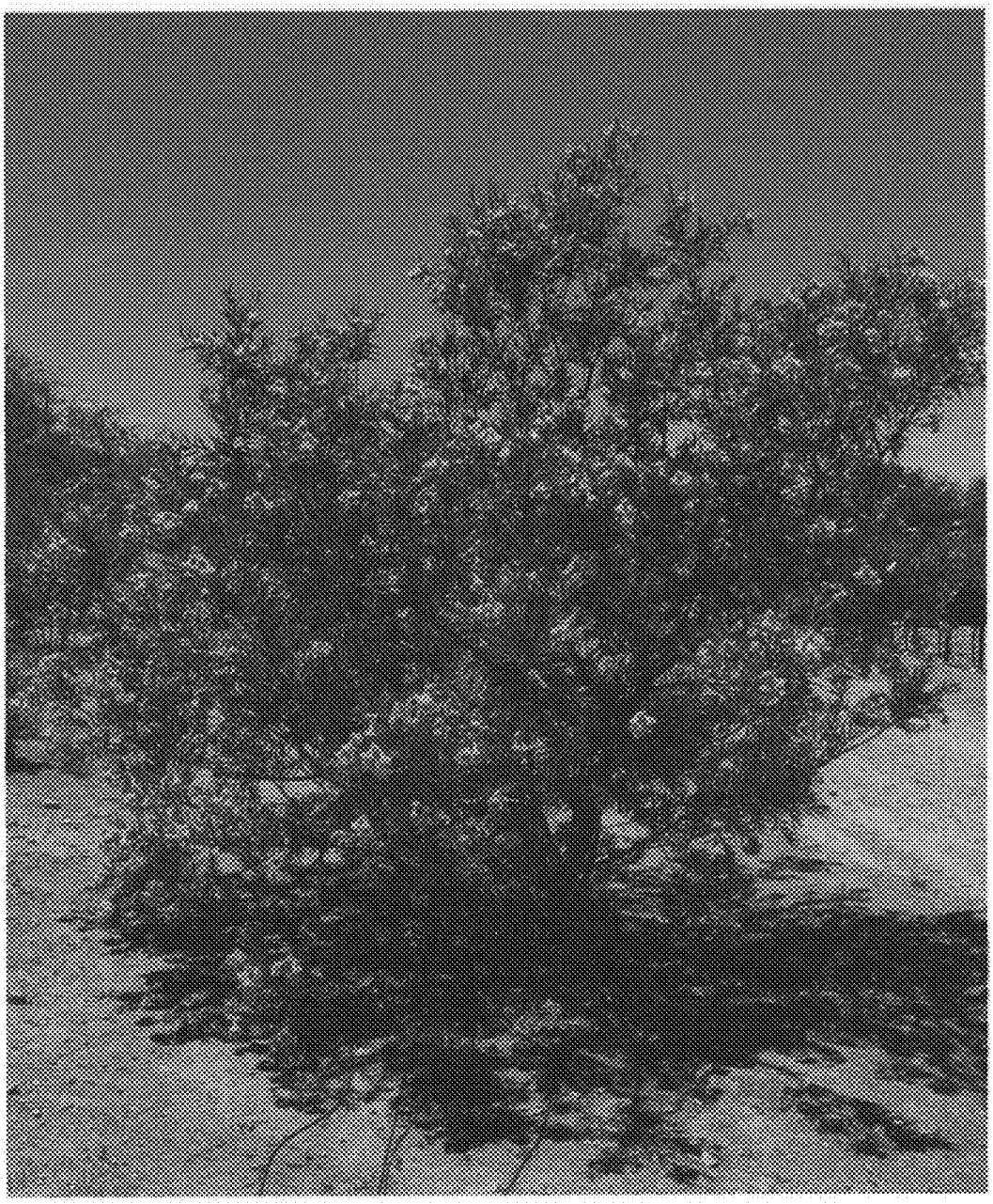
FIG. 1 shows *Chilopsis linearis* 'Bubba Jones' growing as a multitrunked tree.
Figure 2:
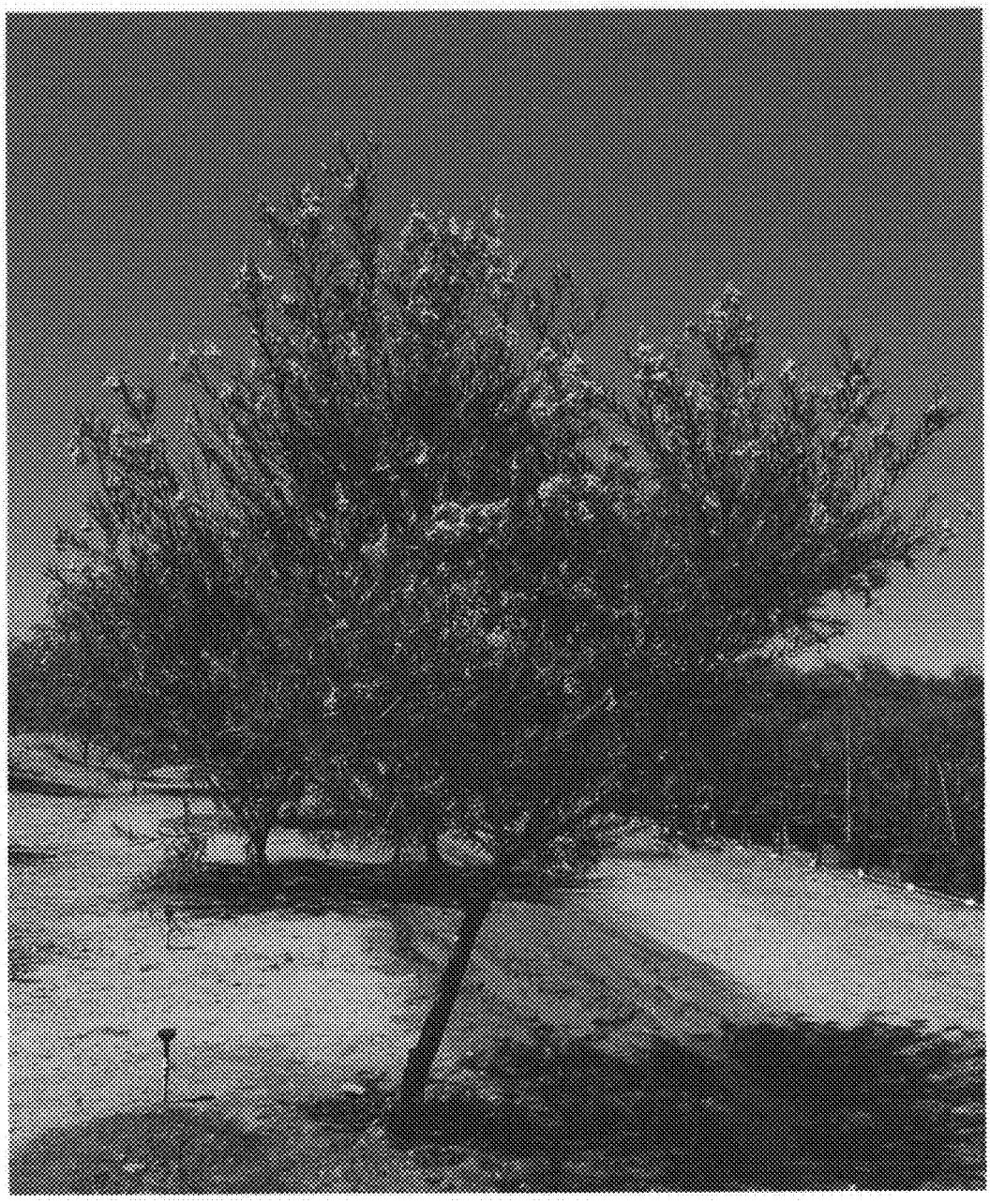
FIG. 2 shows *Chilopsis linearis* 'Bubba Jones' pruned as a standard tree.
Figure 3:
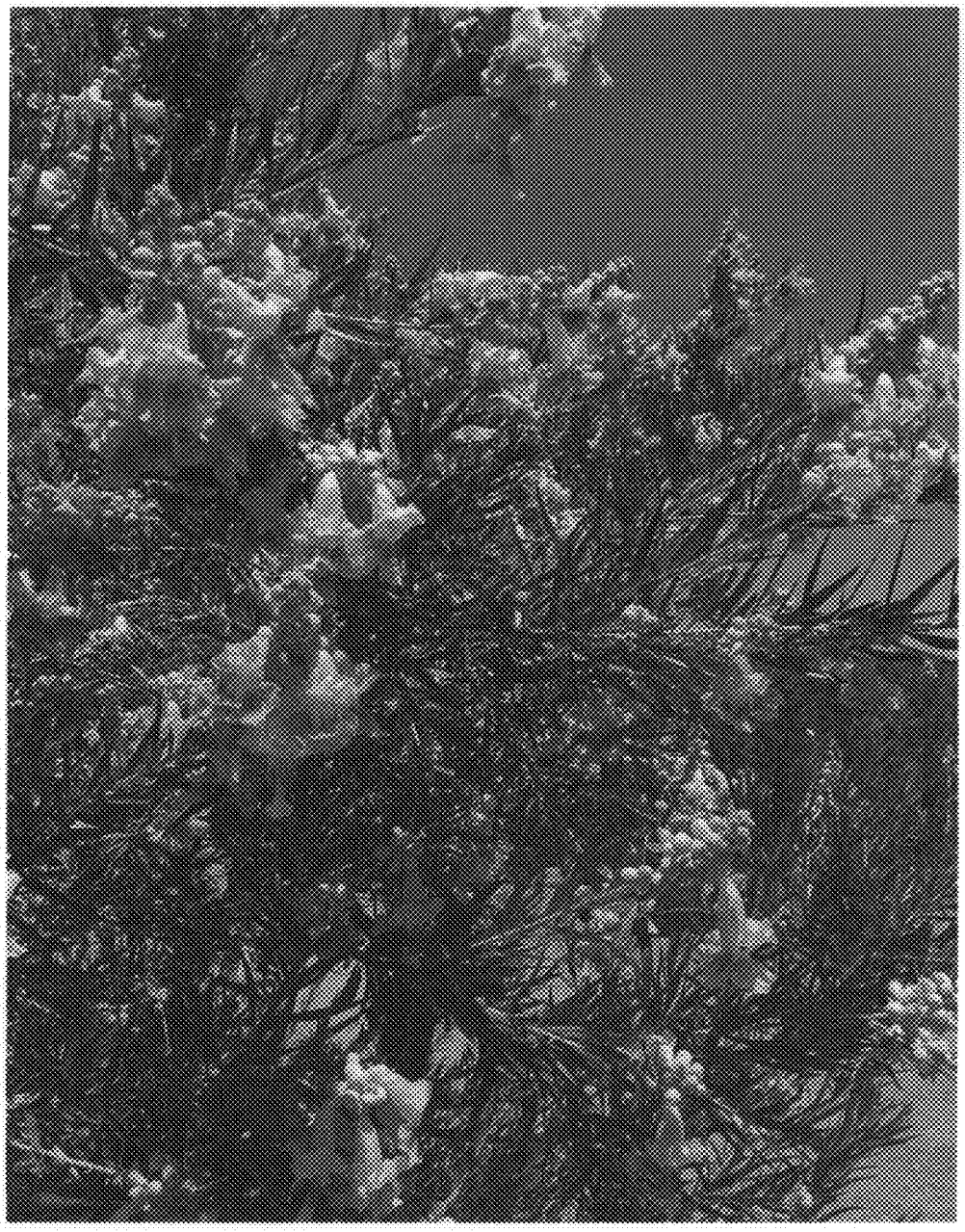
FIG. 3 shows leaves, stems and flowering clusters of *Chilopsis linearis* 'Bubba Jones'.
Figure 4:
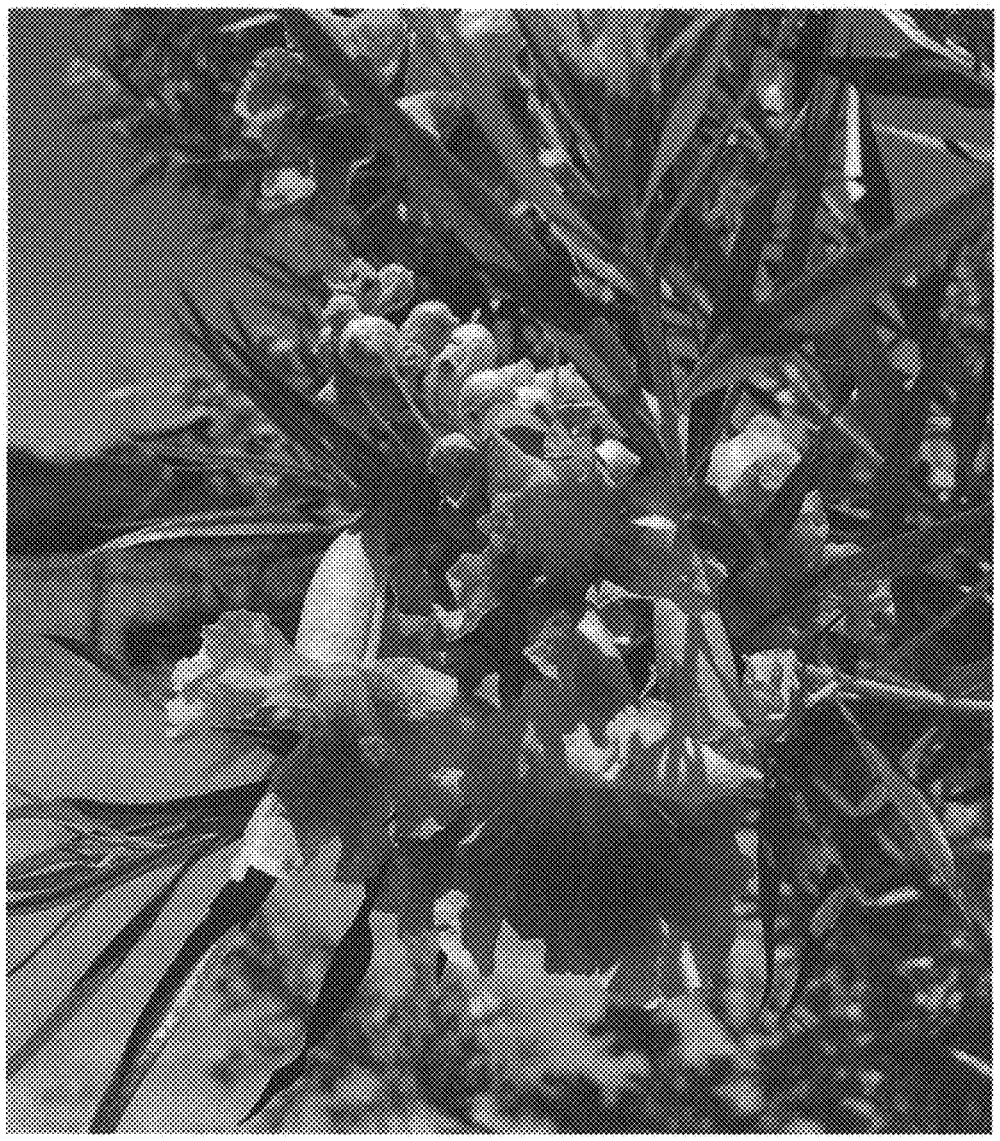
FIG. 4 is a closeup of the inflorescence and flowers of *Chilopsis linearis* 'Bubba Jones'.
Figure 5:
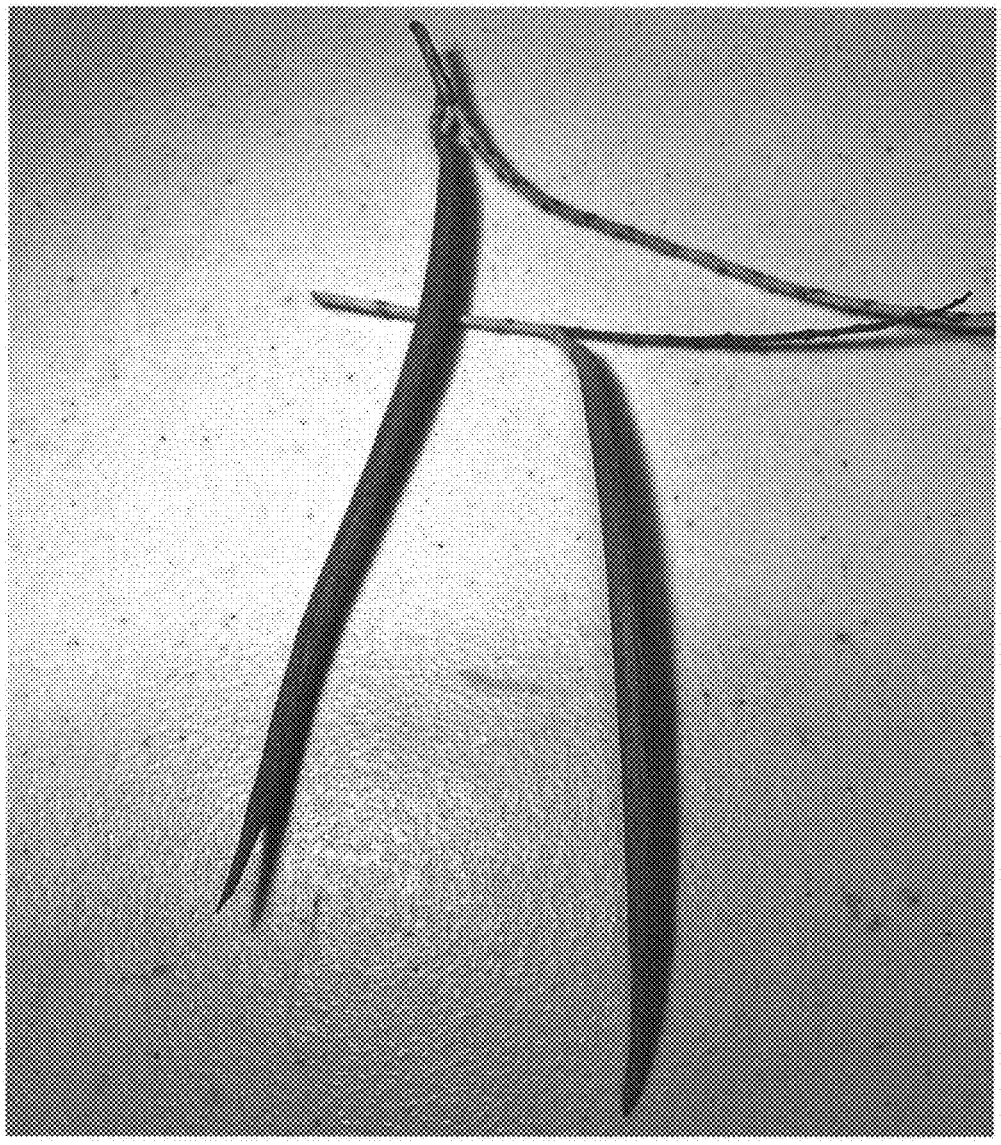
FIG. 5 shows the mature, but still green fruits of *Chilopsis linearis* 'Bubba Jones'.
Figure 6:
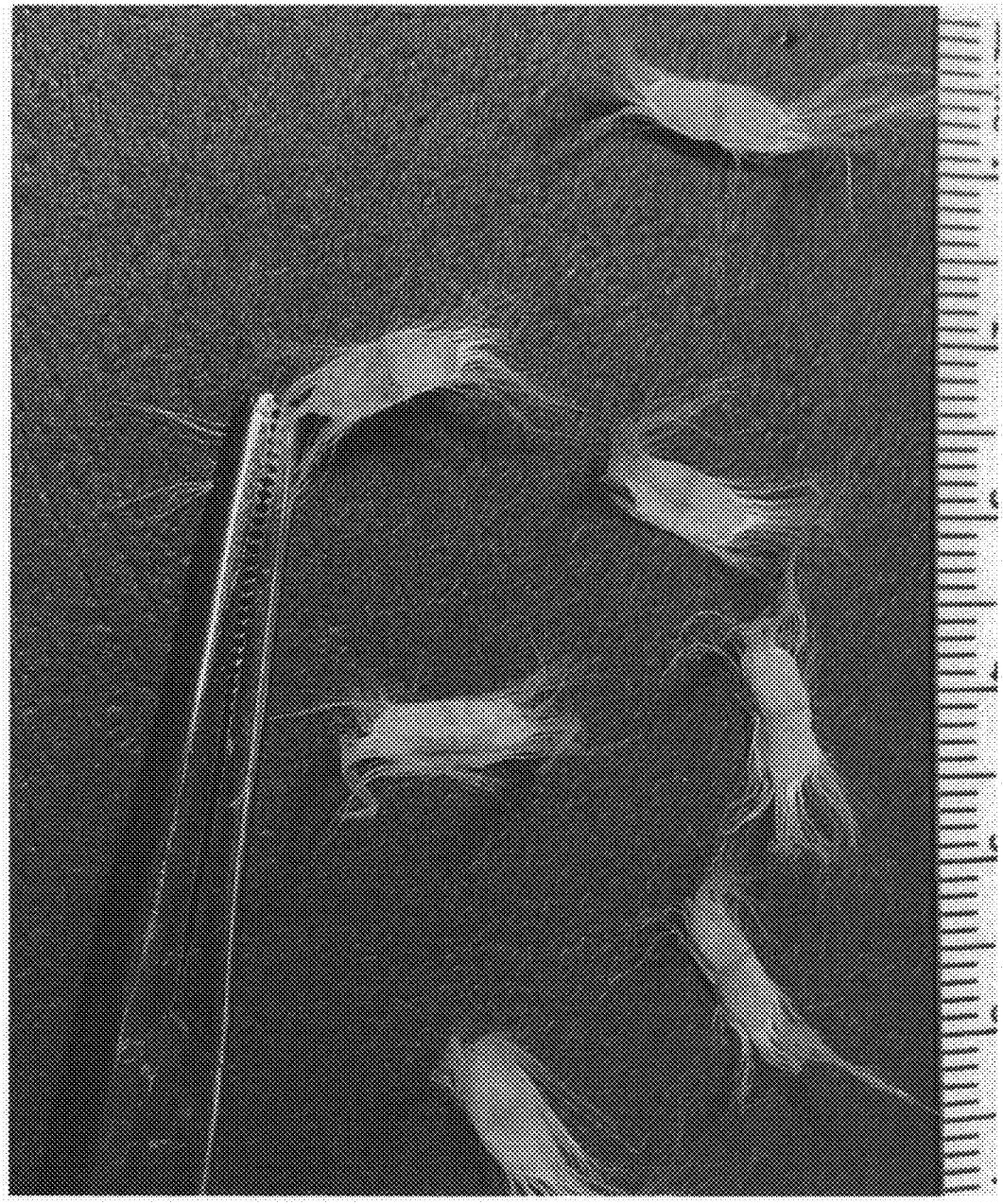
FIG. 6 shows the seeds of *Chilopsis linearis* 'Bubba Jones'.

The following is a detailed description of the new desert willow tree based upon examination and measurements of the original specimen at age 6 years growing in the ground at a commercial plant nursery near Sahuarita, Ariz. The color descriptions are based upon the 5$^{th}$ edition R.H.S. Colour Chart, 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

The 'Bubba Jones' specimen at age 6 years is a small multitrunked tree about 15 feet tall×11 feet wide. Trunk caliper at this age measures 11 cm. Branch angle varies from 30-60°. Bark at this age is still relatively smooth and has not yet developed the rough and cracked surface typical of this tree at maturity. Color on oldest mature stems measuring from 2-110 mm in diameter is 187C. The widely scattered lenticels on older trunks run perpendicular to the axis and measure up to 1 mm wide×3 mm long, color 199D.

Bark on older maturing, terete stems measuring 2-4.5 mm in diameter varies from color 201A-B. Scattered lenticels are present measuring 0.25-1.0 mm long×0.08-0.33 mm wide, color 201C. Maturing young stems are colored 145B with an admixture of 185B on the sunward side. Lenticels are scattered at this age measuring 0.25-1.0 mm long×0.08-0.33 mm wide, colored 201C.

Young, growing stems measure 1.5-2 mm in diameter and are irregularly angular in cross section. Color is N144C. Stems at this stage are covered with very fine ascending straight hairs visible only under magnification, these caducous by maturity.

Leaves are mostly alternate, lanceolate, acute both apically and basally, sessile with a basal pulvinus, glabrous, glossy (sub viscid) on both surfaces. Abaxial leaf surface has slightly raised veins, the veins colored 194C, reticulate. Adaxial veins less prominent, colored 194A. Both leaf surfaces colored alike, 146A on mature leaves. Mature leaves measure 25-96 mm long×5-13 mm wide. Young, growing leaves are colored closest to 144A.

Leaf pulvinus is horizontally elliptical in cross section, measuring 1.5-2.0 mm long ×1 mm thick×1.5 mm wide colored 194A on mature leaves.

Axillary buds are inconspicuous to invisible, measuring less than 0.5 mm colored 194A but gradually darkening to 164A with age. Internode lengths vary from 2-25 mm Inflorescence is a reduced panicle, which on superficial examination appears to be a raceme. Inflorescence measures up to 22 (3-22) cm long×12 (6-12) cm wide. Inflorescence axis measures 2-3 mm in diameter basally tapering to 1.5 mm in diameter apically. Peduncle is 4-12 mm long×2-3 mm in diameter. The surface is covered with wooly hairs that are gradually caducous. Peduncle is colored 145C. Mature inflorescence axis colored from 145B-C. Each inflorescence contains from 7 to 50 flowers each, with 0 to 12 flowers visible on any given day. Individual flowers last from 2-3 days and fall away soon after blooming.

Flower buds are more or less obovoid, 12-13 mm long× 8-9 mm in diameter just before anthesis. A small somewhat obtusely pointed bump (1 mm diameter×0.5 mm high) is visible at the apex of the flower bud. Bud surface tomentulose, the hairs less dense near the bud apex. Bud color close to 157A spotted with 145A, the spots round and measuring about 0.4 mm in diameter. The spots are most heavily concentrated around the widest part of the bud.

Flower bracts measure 5-6 mm long×1.6-2.0 mm wide, more or less lanceolate in shape. Abaxial surface is tomentulose, adaxial surface covered with appressed hairs. Floral bracts are paired, located near the midpoint of the pedicel, which measures 4-5 mm long×1.25 mm diameter.

Pedicel color is 145C. Pedicels are tomentulose, the hairs caducous near anthesis. Bract color is 145C spotted with 145A on the abaxial side, these most concentrated about ⅔ of the way up from the bract base. Bracts are caducous before anthesis.

Calyx comprised of 5 more or less fused sepals, totally enclosing the other floral parts in bud. The fused calyx ruptures at anthesis, usually on 2 or 3 lines, then appearing more or less bilabiate, opening on the lateral edges about ⅓-½ the length from the apex. Calyx color is 157A with scattered spots of 145A, these most heavily concentrated at the widest portion of the bud (about ⅔ of the way up from the bud base). Calyx is covered with tomentulose hairs abaxially, less so near the apex, covered with scattered appressed hairs adaxially, the exterior hairs becoming largely caducous after anthesis. The corolla expands rapidly after breaking through the calyx, from a tightly folded and packed condition inside the unopened bud. Corolla color during expansion is a uniform color 64D.

Flowers measure 56-63 mm long×41 mm high×41-46 mm wide, are trumpet shaped, comprised of 5 mostly fused petals, the tube descending at the calyx then flaring unequally at the limb, bilabiate, the lower 3 corolla lobes extending further than the upper 2. The corolla is glabrous except on the interior tube ridges. The corolla tube is more or less linear for about 10 mm from the receptacle and colored close to 157D. The tube then flares for about 12 mm, becoming nearly parallel until the petal flare at about 40 mm from the base. Most of the corolla is colored 75A, both on the interior and exterior portions with the exception of the basal tube (color 157D), exterior underside of the corolla tube (color 76C), upper interior portion of tube and interior tube immediately adjacent to the ridges (color 65D), interior guidelines (color 72A) and lower petal blotches (color 72A) and the raised ridges on the lower interior portion of the floral tube (color 20A). The colors listed above grade into each other at their margins. The corolla is crisped and ruffled, the margins slightly undulate. Lower corolla lobes are more or less orbicular in shape, somewhat extended and rolled down and back along the margins, measuring 20 mm wide×20 mm long. The interior guidelines mentioned above are concentrated on the lower half of the interior of the floral tube and spread out at the flower limb into irregularly shaped blotches in the lower petal lobes. Color of both the guidelines and blotches is 72A. Upper petal lobes are crisped, more or less orbicular with a slightly undulate margin, measuring 15 mm long×20 mm wide. These petal lobes are crisped, backrolled and somewhat reflexed, color 75A. Inside the floral tube on the lower side are two ridges formed by the longitudinal invagination into the tube, these seen as indentations when viewed from the flower exterior. These ridges begin close to the floral basal flare where they measure 1.5 mm wide×1 mm high. The ridges become larger and gradually diverge as they reach and terminate near the limb of the flower where they measure 3 mm wide×3 mm high. These ridges are scattered with fine, clear wooly hairs up to 2 mm long. The ridges are colored close to 20A. Flowers last about 2-3 days. The corolla is deciduous at the floral disc soon after fading.

The floral disc (receptacle) is nectiferous, spheroidal in shape with a diameter of 2.5 mm. The floral disc is colored 145A.

Flowers have 4 epipetalous stamens and one staminode, the stamens of 2 lengths, the upper 2 shorter than the lower 2. The staminode attachment is located between the upper stamens. Long stamens are 27 mm long, while the short stamens measure 20 mm long. Filaments measure about 1 mm diameter at the base tapering to about 0.5 mm just below the anthers. Filaments are colored 157D. Anthers are basifixed, explanate to somewhat reflexed, measuring 4.5-5 mm long×2-2.3 mm wide. Undehisced anthers measure 3.5 mm long×3 mm wide×1.5 mm thick colored 158D Dehisced anthers and pollen are colored 155C. Staminode measures 16 mm long×0.5 mm diameter, color 157D.

The pistil is single, comprised of 2 carpels. Pistil measures 27.5 mm long. Ovary measures 2.5 mm long×1.5 mm wide, oblongoid in shape, color 154D. Style measures 23 mm long×0.5 mm diameter, terete, somewhat flattened laterally near the stigma, color 157D. Stigma measures 2 mm long×1.5 mm wide×0.2 mm thick when closed, slightly obovate, color 157D. The stigma is doubled and flaring at anthesis, sensitive, closing when touched.

Flowers last about 2-3 days. The corolla is deciduous at the floral disc soon after fading. Flowers are noticeably and pleasantly fragrant.

Fruit and seeds: the fruit of *Chilopsis linearis* 'Bubba Jones' is a many-seeded silique. Fruits are terete and lineoid, tapered at both ends, the pods variously somewhat curved, measuring 12.5-19 cm long×5-7 mm in diameter. Mature fruits are glabrous, longitudinally finely ridged. Fruit apex is apiculate, base acute, but somewhat bulging at the connection with the pedicel. The color of mature fruits is 138B. Some pods, especially those exposed to full sun are tinged with and grade to N77A on the sunward side. The terete pedicel of the mature fruit measures 2 mm in diameter and 5 mm long, color 145C. The pedicels are covered with wooly hairs, densest immediately adjacent to the fruit attachment. When the pods dry the color changes to 165C. By the time the fruit is fully ripened and dry most of the pedicellar hairs have fallen or weathered away. The fruits are tardily and weakly dehiscent. A septum runs the interior length matching the shape of the surrounding fruit. The flattened septum measures 5 mm wide at the widest part of the septum, color 200B. Funicular scars are visible alternating down near the edges and on both sides of the septum.

The ripe fruit examined contained 92 seeds. The seeds are dorsally flattened and translucent; the flat surfaces are glabrous with a ridge line raised perpendicular to the long axis of the seed extending across the seed from the hilum. Ridge color is 164A. Seed margin is ciliate with numerous fine, white hairs which are longest at both ends of each seed. Seed base color is 161D. Seeds measure 8-11 mm long×4 mm wide×200 microns thick exclusive of hairs. Hairs measure from 1 mm to 14 mm in length×less than 50 microns in diameter. The hairs are somewhat crooked, curling as a group to the abaxial side of the seed. The hilum of the seed is shifted to one side of the adaxial surface of the seed. The hilum is irregularly rounded measuring 1 mm long×0.6 mm wide. Hilum color is N199B. On the adaxial side of the seed, fine ridges radiate fanlike across the seed face from the hilum. On the abaxial side of the seed fine ridges run parallel to the seed long axis and are visible microscopically. 'Bubba Jones' has low fruit production, producing about 20 pods/year, at least under the growing conditions present in Sahuarita, Ariz. Other cultivars of *Chilopsis* produced from zero to many fruits under identical growing conditions.

No pests or diseases have been noted on 'Bubba Jones'.

COMPARISONS TO RELATED *CHILOPSIS*

Compared to its maternal parent, 'Bubba', 'Bubba Jones' is more open growing and has bicolored flowers somewhat similar in appearance to those of 'Bubba' but much larger. Compared to its paternal parent, 'Warren Jones', 'Bubba Jones' has bicolored ruffled flowers compared to pink ruffled flowers on 'Warren Jones'. 'Warren Jones' produces a more or less normal (for the species) amount of fruits and seeds while 'Bubba Jones' produces few fruits and seeds. 'Bubba' is few fruited and is similar to 'Bubba Jones' in this aspect. Corollas of 'Bubba Jones' are more crisped than those of 'Bubba'. The flowers of 'Bubba Jones' would generally be considered bicolored.

There are numerous named and a couple of patented cultivars of *Chilopsis linearis*. Many of the named cultivars have gone out of cultivation and those will not be discussed here. The majority of the remaining cultivars can easily be distinguished by flower color, vigor, and growth form. Other useful characters will be included if helpful for distinguishing the cultivars. Cultivars listed without patent numbers are unpatented.

The following cultivars may be separated on the basis of flower color alone:

More or less monochromatic flower cultivars: 'Paradise' has pink flowers. 'Tejas' has pink to reddish purple flowers. Cultivars 'Rio Salado' and 'AZT Amethyst' have burgundy flowers. 'Hope' has white flowers with a yellow throat. 'AZT Dora's Desert Rose' has pink flowers. 'Mesquite Valley Pink' is the same plant as 'Pink Star', which has ruffled dark pink flowers with a yellow throat. 'White Storm' has white flowers. 'Alpine' has large, pink flowers.

Cultivars with bicolored flowers: 'Barranco' has pink over maroon flowers. Specifically, compared to 'Bubba Jones', the flower main color is a bit lighter for 'Barranco', while the lower petal blotches are similar in color to those of 'Bubba Jones', the blotches cover more of the lower petal lobes and are almost reticulately distributed over the petal lobe surface, while those of 'Bubba Jones' are more uniform in appearance and do not extend to the margins of the petal lobes.

The petal lobes of 'Barranco' are also less backrolled and ruffled than those of 'Bubba Jones'. 'Art's Seedless' has pink over burgundy flowers. 'Art's Seedless' may be further distinguished by the overall flower color being lighter than that of 'Bubba Jones' and the lower petal lobes (Art's Seedless) are uniformly burgundy compared to 'Bubba Jones' lower petal lobes with blotches of color similar to 'Art's Seedless' but only covering part of the lower petal lobes. 'AZT Bi-color' has pink over maroon flowers very similar in color and pattern to 'Art's Seedless' and may be similarly distinguished from 'Bubba Jones' on this basis. 'Regal' has lavender over wine red flowers. 'Burgundy' is the same plant as 'Burgundy Lace' and has white-pink over pink-magenta flowers. 'Dark Storm' has lavender over wine red flowers. 'Lois Adams' has pale lavender over magenta flowers. 'Marfa Lace' has semi-double flowers colored pink over rose.

'Lucretia Hamilton' has bicolored flowers with wine over maroon and also produces reduced amounts of fruits.

Patented and patent applied for cultivars: 'Monhews' (U.S. Plant Pat. No. 11,078) is the same plant as 'Timeless Beauty' and has lavender (color 76D) over burgundy (color 77A) flowers. 'MSWNLopur' (U.S. Plant Pat. No. 28,902) has a different flower color N79A-B (more or less monochromatic) compared to 'Bubba Jones' bicolored 75A over 72A. 'MSWNLopur' is similar to 'Bubba Jones' in leaf color, 146A-B for 'MSWNLopur' compared to 146A for 'Bubba Jones'. 'MSWNLopur' is reported to have opposite leaves while the leaves of 'Bubba Jones' are mostly alternate.

Compared to 'Sweet Bubba' (currently under patent evaluation), the flowers of 'Bubba Jones' are 1.5 times as large. 'Sweet Bubba' has nearly monochromatic flowers, color 70A while 'Bubba Jones' has bicolored flowers, color 75A over 72A which are more ruffled than those of 'Sweet Bubba'. The growth form of 'Bubba Jones' is more open than that of 'Sweet Bubba'.

I claim:

1. A new and distinct *Chilopsis linearis* tree substantially as described and illustrated herein.

* * * * *